United States Patent
Hitz et al.

(10) Patent No.: US 6,812,382 B1
(45) Date of Patent: Nov. 2, 2004

(54) PLANT GENES ENCODING CHLOROPLAST DIVISION PROTEINS

(75) Inventors: William D. Hitz, Wilmington, DE (US); Guo-Hua Miao, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/500,495

(22) Filed: Feb. 9, 2000

Related U.S. Application Data

(60) Provisional application No. 60/119,419, filed on Feb. 10, 1999.

(51) Int. Cl.[7] .......................... A01H 3/00; C07H 21/04; C07K 14/415; C12N 5/14; C12N 9/00
(52) U.S. Cl. .......................... 800/295; 435/6; 435/69.1; 435/183; 435/410; 435/419; 435/252.3; 435/320.1; 530/370; 536/23.1; 536/23.2; 536/23.6; 536/24.1; 536/24.3; 536/24.33; 536/24.5; 800/278
(58) Field of Search ........................... 435/6, 69.1, 183, 435/410, 419, 252.3, 320.1; 530/370; 536/23.1, 23.2, 23.6, 24.1, 24.3, 24.33, 24.5; 800/278, 295

(56) References Cited

U.S. PATENT DOCUMENTS 5,349,123 A * 9/1994 Shewmaker et al.
5,981,836 A 11/1999 Osteryoung

FOREIGN PATENT DOCUMENTS

WO   WO 98/00436   8/1998

OTHER PUBLICATIONS

Bork, P. Genome Research. vol. 10, p. 398–400, 2000.*
Mullet, J. E. (1988) Annu. Rev. Plant Phys. Plant Mol. Biol. 39:475–502.
Kuroiwa, T. et al., (1988) Int. Rev. Cyto. 181:1–41.
Pyke, K. A. (1997) Am. J. Bot. 84:1017–1027.
Osteryoung, K. W. et al., (1995) Nature 376:473–474.
Osteryoung, K. W. et al., (1998) The Plant Cell 10:1991–2004.
Strepp, R. et al., (1998) PNAS 95:4368–4373.
NCBI General Identifier No. 2494610.
NCBI General Identifier No. 3116020.
NCBI General Identifier No. 3608495.
NCBI General Identifier No. 6685070.

* cited by examiner

Primary Examiner—Phuong T. Bui

(57) ABSTRACT

This invention relates to an isolated nucleic acid fragment encoding a protein involved in plastid division. The invention also relates to the construction of a chimeric gene encoding all or a portion of the protein involved in plastid division, in sense or antisense orientation, wherein expression of the chimeric gene results in production of altered levels of the protein involved in plastid division in a transformed host cell.

11 Claims, No Drawings

SEQUENCE LISTING

<160> NUMBER OF SEQ ID NOS: 24

<210> SEQ ID NO 1
<211> LENGTH: 447
<212> TYPE: DNA
<213> ORGANISM: Zea mays

<400> SEQUENCE: 1

```
agtggccatg gcgtcatccg ccgccgccgc ctcctcggct tccgcgctct tccgcctccc      60
ggggtcgggc cacctgcgtg caccgccacg aagcgggtgg cgagaccaca ggcggtcccg     120
tcgcgcgacc gtgcggtgct cgttcgcgcc ggtggagacg gcccggataa aggtggtggg     180
cgttggcgga ggcggcaaca acgccgtcaa ccgcatgatc ggcagcggcc tccagggcat     240
cgaattttat gctataaaca ccgattccca agcccttatt aattcacaag cgcaatatcc     300
tctgcaaatt ggagagcagt tgacccgcgg cttaagtgcc ggtggaaatc cgaatttggg     360
agagcaggct gctgaggaat caagagtaaa ccatagccac tgccctgaag gattcagatc     420
ttgtcttcat aacagctggg aatggga                                         447
```

<210> SEQ ID NO 2
<211> LENGTH: 148
<212> TYPE: PRT
<213> ORGANISM: Zea mays

<400> SEQUENCE: 2

```
Val Ala Met Ala Ser Ser Ala Ala Ala Ser Ser Ala Ser Ala Leu
  1               5                  10                  15
Phe Arg Leu Pro Gly Ser Gly His Leu Arg Ala Pro Pro Arg Ser Gly
                 20                  25                  30
Trp Arg Asp His Arg Arg Ser Arg Arg Ala Thr Val Arg Cys Ser Phe
             35                  40                  45
Ala Pro Val Glu Thr Ala Arg Ile Lys Val Val Gly Val Gly Gly Gly
         50                  55                  60
Gly Asn Asn Ala Val Asn Arg Met Ile Gly Ser Gly Leu Gln Gly Ile
 65                  70                  75                  80
Glu Phe Tyr Ala Ile Asn Thr Asp Ser Gln Ala Leu Ile Asn Ser Gln
                 85                  90                  95
Ala Gln Tyr Pro Leu Gln Ile Gly Glu Gln Leu Thr Arg Gly Leu Ser
                100                 105                 110
Ala Gly Gly Asn Pro Asn Leu Gly Glu Gln Ala Ala Glu Glu Ser Arg
            115                 120                 125
Val Asn His Ser His Cys Pro Glu Gly Phe Arg Ser Cys Leu His Asn
        130                 135                 140
Ser Trp Glu Trp
145
```

<210> SEQ ID NO 3
<211> LENGTH: 1427
<212> TYPE: DNA
<213> ORGANISM: Glycine max

<400> SEQUENCE: 3

```
gcacgagcga tgcttcatcc cctcacaaac ccaaacgcaa acgagcttct ctcactctca      60
tgctcttcta tattccacca caatgcactc acaacctccg tttctctcaa ccccagaaca     120
acaaaaattg ctcctcaacg cctaagtcgt cgtttcgggt ccgtgagatg ctcttacgct     180
```

-continued

```
tacgtagata acgccaaaat taaggttgtc ggcatcggtg gtggcggcaa caatgccgtt    240
aatcgcatga tcggtagtgg tttgcagggt gtagacttct atgcaataaa taccgatgct    300
caggcactgt taaattctgc tgctgagaac cctattaaaa ttggagaagt tctgactcgt    360
ggattaggta cgggcgggaa tccactttg ggggaacaag ctgcagagga atcaagagat     420
gctattgctg atgctcttaa aggatcagat ttggtgttta acggctgg gatgggtggg      480
ggaaccgggt ctggtgctgc cccagttgta gcccaaatat caaaagaggc aggttacttg    540
actgtaggtg ttgttaccta tcccttcagt tttgaaggac gtaagagatc cttgcaggcc    600
tttgaagcca tcgaaaggct gcagaaaaat gttgacacac ttatagtgat tccaaatgac    660
cgtctgcttg acatagctga tgagcagatg cctcttcagg atgctttccg tcttgcagat    720
gacgttctac ggcaaggagt acagggaata tcagacatta taactgtacc tggacttgtc    780
aatgtggatt ttgcagatgt aaaagctgtg atgaaagact ctgggactgc aatgcttgga    840
gtaggtgttt cctccggtaa aaaccgagca gaagaagcag ccgaacaggc tactttggct    900
cctttaattg gatcctctat tcagtcagct actggggtag tgtataatat tactggagga    960
aaggacataa ccctgcagga agtgaacagg gtttctcagg ttgtgactag tttggctgat    1020
ccttctgcta atattatatt tggggctgtc gttgatgatc gctacacggg ggagattcac    1080
gtgactatca ttgcaactgg cttctcacag tcttttcaga agaagttgct aacagatcca    1140
agggctgcaa agctgcttga caaggtggct gagggccaag aaagcaaggc agtccctcct    1200
cccctcaagt cctcaaacaa ggttgaatct agaccatccc cgcgaaagct cttttttttag   1260
ttgcatggtt cttttaccc tttttcattt ttccaattat tattattata ttatattggc     1320
cgatcaaaaa aaaattatt atattatatt gtaggacaca atgatcttga tgcttaatta     1380
agtgagatat cattctcttg atgttcaaaa aaaaaaaaaa aaaaaa                   1427
```

<210> SEQ ID NO 4
<211> LENGTH: 419
<212> TYPE: PRT
<213> ORGANISM: Glycine max

<400> SEQUENCE: 4

```
Ala Arg Ala Met Leu His Pro Leu Thr Asn Pro Asn Ala Asn Glu Leu
  1               5                  10                  15

Leu Ser Leu Ser Cys Ser Ser Ile Phe His His Asn Ala Leu Thr Thr
             20                  25                  30

Ser Val Ser Leu Asn Pro Arg Thr Thr Lys Ile Ala Pro Gln Arg Leu
         35                  40                  45

Ser Arg Arg Phe Gly Ser Val Arg Cys Ser Tyr Ala Tyr Val Asp Asn
     50                  55                  60

Ala Lys Ile Lys Val Val Gly Ile Gly Gly Gly Asn Asn Ala Val
 65                  70                  75                  80

Asn Arg Met Ile Gly Ser Gly Leu Gln Gly Val Asp Phe Tyr Ala Ile
                 85                  90                  95

Asn Thr Asp Ala Gln Ala Leu Leu Asn Ser Ala Ala Glu Asn Pro Ile
            100                 105                 110

Lys Ile Gly Glu Val Leu Thr Arg Gly Leu Gly Thr Gly Asn Pro
        115                 120                 125

Leu Leu Gly Glu Gln Ala Ala Glu Glu Ser Arg Asp Ala Ile Ala Asp
    130                 135                 140

Ala Leu Lys Gly Ser Asp Leu Val Phe Ile Thr Ala Gly Met Gly Gly
```

```
                145                 150                 155                 160
Gly Thr Gly Ser Gly Ala Ala Pro Val Val Ala Gln Ile Ser Lys Glu
                    165                 170                 175
Ala Gly Tyr Leu Thr Val Gly Val Val Thr Tyr Pro Phe Ser Phe Glu
                    180                 185                 190
Gly Arg Lys Arg Ser Leu Gln Ala Phe Glu Ala Ile Glu Arg Leu Gln
                    195                 200                 205
Lys Asn Val Asp Thr Leu Ile Val Ile Pro Asn Asp Arg Leu Leu Asp
                    210                 215                 220
Ile Ala Asp Glu Gln Met Pro Leu Gln Asp Ala Phe Arg Leu Ala Asp
225                 230                 235                 240
Asp Val Leu Arg Gln Gly Val Gln Gly Ile Ser Asp Ile Ile Thr Val
                    245                 250                 255
Pro Gly Leu Val Asn Val Asp Phe Ala Asp Val Lys Ala Val Met Lys
                    260                 265                 270
Asp Ser Gly Thr Ala Met Leu Gly Val Gly Val Ser Ser Gly Lys Asn
                    275                 280                 285
Arg Ala Glu Glu Ala Ala Glu Gln Ala Thr Leu Ala Pro Leu Ile Gly
                    290                 295                 300
Ser Ser Ile Gln Ser Ala Thr Gly Val Val Tyr Asn Ile Thr Gly Gly
305                 310                 315                 320
Lys Asp Ile Thr Leu Gln Glu Val Asn Arg Val Ser Gln Val Val Thr
                    325                 330                 335
Ser Leu Ala Asp Pro Ser Ala Asn Ile Ile Phe Gly Ala Val Val Asp
                    340                 345                 350
Asp Arg Tyr Thr Gly Glu Ile His Val Thr Ile Ile Ala Thr Gly Phe
                    355                 360                 365
Ser Gln Ser Phe Gln Lys Lys Leu Leu Thr Asp Pro Arg Ala Ala Lys
                    370                 375                 380
Leu Leu Asp Lys Val Ala Glu Gly Gln Glu Ser Lys Ala Val Pro Pro
385                 390                 395                 400
Pro Leu Lys Ser Ser Asn Lys Val Glu Ser Arg Pro Ser Pro Arg Lys
                    405                 410                 415
Leu Phe Phe

<210> SEQ ID NO 5
<211> LENGTH: 1560
<212> TYPE: DNA
<213> ORGANISM: Triticum aestivum

<400> SEQUENCE: 5
gcacgagcct cccctctcct cccggccacc tctccccacg cccattcccc gcacggccaa      60
gggaaaatgg cgccgtccac ctcgtcggcc tccgccctcc tccacctccc gggtctgcct     120
ccccggggac cccatagagg cgggtgccgg aaccaccgc ggcggccgcg ccatgcggcc      180
gtgcggtgct ccttcgcgtt cgcgcccgtg agacggcga ggataaaggt cgtgggcgta      240
ggtggcggcg gcaacaacgc cgtcaaccgc atgatcggca cggcctcca gggaatcgag      300 ttttatgcta taaacacaga ctcccaggct cttgtgaatt cccaggcgca acatccgcta     360
caaattggag aacaattgac tcgtgggctg gtactggtg aaatcctaa tttgggagaa      420 caagctgccg aggaatcaaa ggaagtgata gctaatgccc tccgagattc tgaccttgtc     480
ttcataacag ctgggatggg aggtggtact ggctccggtg ctgctccagt tgttgcccag     540
atagcaaagg aggccggtta tcttactgtc ggtgttgtca cctacccatt cagcttcgaa     600
```

-continued

```
ggacgcaagc gctctctaca ggcactcgaa gcattggaga agcttgaaag aagtgttgac    660
actctgattg tgattccaaa tgatcggttg ttagatattg ctgatgagaa tatgcccttg    720
caagacgcat ttctcctggc agatgatgtc cttcgacagg gtgtccaagg aatatcagac    780
attatcacga tacctgggct cgtgaatgtt gattttgctg atgtgaaagc tgtgatgaaa    840
aattctggaa ctgccatgct cggagttggt gtttcttcca gcaaaaaccg tgcccaagaa    900
gctgctgagc aggcaactct tgccccttg ataggggtcat ccattgaggc agctactggt    960
gtcgtgtaca acatcactgg tgggaaggac atcacttta c aagaagtgaa caaggtctct   1020
cagatcgtga aagcttggc tgatccctcg gcaaacataa ttttcggagc tgtggtcgac   1080
gaccgttata acggcgagat ccacgtgacc atcatcgcaa caggatttcc gcagtccttc   1140
cagaagtccc ttctggctga cccgaaggga gcacggatac tggaggcgaa agaaaaagtg   1200
gctagcctcg caacgctgc tgcggcgcaa caaccggcgg tggccgtccc gacatggtcc   1260
cggaggctct tctcctgaac actgttcagc aggcaaacaa ccttgcgatt gtgaggctgt   1320
ggttctcact ttctcgaggc agtagagatt tttagccggt gttattcttt ttggccgtgt   1380
aaacactctt aaaactagtt ttgcgtagtg attaggttcc cgcctagtgt atgtattgtt   1440
cagacacttg actcggttgg tttagaaagt gttctgttcg ttgacagctt tggcaaaaaa   1500
aaaaaaaaaa aaaaaaaaaa aaaaaaaaaa aaaaaaaaaa aaaaaaaaaa aaaaaaaaaa   1560
```

<210> SEQ ID NO 6
<211> LENGTH: 425
<212> TYPE: PRT
<213> ORGANISM: Triticum aestivum

<400> SEQUENCE: 6

```
Ala Arg Ala Ser Pro Leu Leu Pro Ala Thr Ser Pro His Ala His Ser
  1               5                  10                  15

Pro His Gly Gln Gly Lys Met Ala Pro Ser Thr Ser Ser Ala Ser Ala
             20                  25                  30

Leu Leu His Leu Pro Gly Leu Pro Pro Arg Gly Pro His Arg Gly Gly
         35                  40                  45

Cys Arg Asn His Pro Arg Arg Pro Arg His Ala Ala Val Arg Cys Ser
     50                  55                  60

Phe Ala Phe Ala Pro Val Glu Thr Ala Arg Ile Lys Val Val Gly Val
 65                  70                  75                  80

Gly Gly Gly Gly Asn Asn Ala Val Asn Arg Met Ile Gly Ser Gly Leu
                 85                  90                  95

Gln Gly Ile Glu Phe Tyr Ala Ile Asn Thr Asp Ser Gln Ala Leu Val
            100                 105                 110

Asn Ser Gln Ala Gln His Pro Leu Gln Ile Gly Glu Gln Leu Thr Arg
        115                 120                 125

Gly Leu Gly Thr Gly Gly Asn Pro Asn Leu Gly Glu Gln Ala Ala Glu
    130                 135                 140

Glu Ser Lys Glu Val Ile Ala Asn Ala Leu Arg Asp Ser Asp Leu Val
145                 150                 155                 160

Phe Ile Thr Ala Gly Met Gly Gly Thr Gly Ser Gly Ala Ala Pro
                165                 170                 175

Val Val Ala Gln Ile Ala Lys Glu Ala Gly Tyr Leu Thr Val Gly Val
            180                 185                 190

Val Thr Tyr Pro Phe Ser Phe Glu Gly Arg Lys Arg Ser Leu Gln Ala
        195                 200                 205
```

```
Leu Glu Ala Leu Glu Lys Leu Glu Arg Ser Val Asp Thr Leu Ile Val
    210                 215                 220

Ile Pro Asn Asp Arg Leu Leu Asp Ile Ala Asp Glu Asn Met Pro Leu
225                 230                 235                 240

Gln Asp Ala Phe Leu Leu Ala Asp Asp Val Leu Arg Gln Gly Val Gln
                245                 250                 255

Gly Ile Ser Asp Ile Ile Thr Ile Pro Gly Leu Val Asn Val Asp Phe
            260                 265                 270

Ala Asp Val Lys Ala Val Met Lys Asn Ser Gly Thr Ala Met Leu Gly
            275                 280                 285

Val Gly Val Ser Ser Lys Asn Arg Ala Gln Glu Ala Ala Glu Gln
    290                 295                 300

Ala Thr Leu Ala Pro Leu Ile Gly Ser Ser Ile Glu Ala Ala Thr Gly
305                 310                 315                 320

Val Val Tyr Asn Ile Thr Gly Gly Lys Asp Ile Thr Leu Gln Glu Val
                325                 330                 335

Asn Lys Val Ser Gln Ile Val Thr Ser Leu Ala Asp Pro Ser Ala Asn
                340                 345                 350

Ile Ile Phe Gly Ala Val Val Asp Asp Arg Tyr Asn Gly Glu Ile His
            355                 360                 365

Val Thr Ile Ile Ala Thr Gly Phe Pro Gln Ser Phe Gln Lys Ser Leu
    370                 375                 380

Leu Ala Asp Pro Lys Gly Ala Arg Ile Leu Glu Ala Lys Glu Lys Val
385                 390                 395                 400

Ala Ser Leu Ala Thr Ala Ala Ala Gln Gln Pro Ala Val Ala Val
                405                 410                 415

Pro Thr Trp Ser Arg Arg Leu Phe Ser
                420                 425

<210> SEQ ID NO 7
<211> LENGTH: 436
<212> TYPE: DNA
<213> ORGANISM: Zea mays

<400> SEQUENCE: 7
acccattgaa ccagaaaata ggttacagat tggccaagaa ttgacacgtg gtcttggtgc    60
tggtgggaac ccagaaattg gcatgaatgc agccaaggaa agccaggagt tggtagaaca   120
ggcagttgct ggtgccgata tggttttttgt gacggctgga atgggaggtg ggacaggcac   180
tggtggagca cctattattg cagggattgc aaagtccatg ggtatattga ctgttggaat   240
tgtcacaacc ccattttcat ttgagggaag aaggcgggct cttcaggcac aagaggaat   300 tgcatcgttg agaagcaatg ttgatacact gattgtaatt ccaaatgaca agttactgac   360
tgctgtgtcc ccaaatactc ctgtgacaga agcattcaat ttagcagatg atatctcggc   420
aagggtcgtg ggtaca                                                   436

<210> SEQ ID NO 8
<211> LENGTH: 145
<212> TYPE: PRT
<213> ORGANISM: Zea mays

<400> SEQUENCE: 8

Pro Ile Glu Pro Glu Asn Arg Leu Gln Ile Gly Gln Glu Leu Thr Arg
1               5                   10                  15

Gly Leu Gly Ala Gly Gly Asn Pro Glu Ile Gly Met Asn Ala Ala Lys
```

```
                20                  25                  30
Glu Ser Gln Glu Leu Val Glu Gln Ala Val Ala Gly Ala Asp Met Val
            35                  40                  45

Phe Val Thr Ala Gly Met Gly Gly Thr Gly Thr Gly Gly Ala Pro
 50                  55                  60

Ile Ile Ala Gly Ile Ala Lys Ser Met Gly Ile Leu Thr Val Gly Ile
 65                  70                  75                  80

Val Thr Thr Pro Phe Ser Phe Glu Gly Arg Arg Ala Leu Gln Ala
                85                  90                  95

Gln Glu Gly Ile Ala Ser Leu Arg Ser Asn Val Asp Thr Leu Ile Val
                100                 105                 110

Ile Pro Asn Asp Lys Leu Leu Thr Ala Val Ser Pro Asn Thr Pro Val
                115                 120                 125

Thr Glu Ala Phe Asn Leu Ala Asp Asp Ile Ser Ala Arg Val Val Gly
                130                 135                 140

Thr
145

<210> SEQ ID NO 9
<211> LENGTH: 857
<212> TYPE: DNA
<213> ORGANISM: Oryza sativa

<400> SEQUENCE: 9
gtgtggacac cctcattgtc atcccaaatg acaagctgtt gtctgctgtt tctccaaata      60
ctccagtaac cgaagcattc aacttggctg atgatattct tcgacaagga attcgtggta     120
tctctgatat tatcacggtt cctgggttgg ttaatgttga ttttgctgat gttcgagcca     180
tcatgcaaaa tgcaggctca tccttgatgg gtattggaac ggctacaggg aagtcaagag     240
caagagatgc tgctcttaat gccattcagt caccactgct agacattgga attgaaagag     300
ctacaggcat tgtgtggaat atcactgggg gagctgatat gactttgttt gaggtgaatt     360
ctgctgctga gatcatctat gaccttgttg atccaaatgc taatctgata tttggtgctg     420
tcatagaccc atcactcaat ggccaagtga gcataacctt gattgccact ggcttcaaac     480
gtcaagatga accagaaggt cgcaccacaa agggtggcca acaaacgcaa ggagacaatg     540
gtcgacgccc atcctctgca gaaggcagca tgattgagat tcctgagttc cttcggagga     600
gaggaccttc tcgcttcccg cgagtctgac tgcccaggct cccttccctt gcccagtatc     660
tatgcttatc agcattctcc tagatcagtc gcctcatgta ggataccagg catgtacagt     720
actgtagttg tttggttgtt cagttttgtt tactccctta tgttctatat tttgagatct     780
tactgttaat aatttgtagc aatgagcttg ctaatgctat agaaatcgtt ttatcccaaa     840
aaaaaaaaaa aaaaaaa                                                    857

<210> SEQ ID NO 10
<211> LENGTH: 208
<212> TYPE: PRT
<213> ORGANISM: Oryza sativa

<400> SEQUENCE: 10

Val Asp Thr Leu Ile Val Ile Pro Asn Asp Lys Leu Leu Ser Ala Val
 1               5                   10                  15

Ser Pro Asn Thr Pro Val Thr Glu Ala Phe Asn Leu Ala Asp Asp Ile
                20                  25                  30

Leu Arg Gln Gly Ile Arg Gly Ile Ser Asp Ile Ile Thr Val Pro Gly
```

```
                   35                   40                   45
Leu Val Asn Val Asp Phe Ala Asp Val Arg Ala Ile Met Gln Asn Ala
     50                      55                      60
Gly Ser Ser Leu Met Gly Ile Gly Thr Ala Thr Gly Lys Ser Arg Ala
 65                      70                      75                      80
Arg Asp Ala Ala Leu Asn Ala Ile Gln Ser Pro Leu Leu Asp Ile Gly
                 85                      90                      95
Ile Glu Arg Ala Thr Gly Ile Val Trp Asn Ile Thr Gly Gly Ala Asp
                    100                     105                     110
Met Thr Leu Phe Glu Val Asn Ser Ala Ala Glu Ile Ile Tyr Asp Leu
                115                     120                     125
Val Asp Pro Asn Ala Asn Leu Ile Phe Gly Ala Val Ile Asp Pro Ser
130                     135                     140
Leu Asn Gly Gln Val Ser Ile Thr Leu Ile Ala Thr Gly Phe Lys Arg
145                     150                     155                     160
Gln Asp Glu Pro Glu Gly Arg Thr Thr Lys Gly Gly Gln Gln Thr Gln
                    165                     170                     175
Gly Asp Asn Gly Arg Arg Pro Ser Ser Ala Glu Gly Ser Met Ile Glu
                180                     185                     190
Ile Pro Glu Phe Leu Arg Arg Arg Gly Pro Ser Arg Phe Pro Arg Val
            195                     200                     205

<210> SEQ ID NO 11
<211> LENGTH: 1059
<212> TYPE: DNA
<213> ORGANISM: Glycine max

<400> SEQUENCE: 11
ttggtattgt caccacccct ttctcgtttg aagggagaaa gagatctatt caagcccaag      60
aaggaattac agccttaaga gataatgttg acacgcttat agttattcca atgacaagc     120
tactaacggc agtttctcaa tctaccctg taactgaagc attcaatctg ctgatgata     180
ttcttcgaca gggtgttcgt ggcatatctg atattattac ataccaggg ttggtgaatg     240
tagattttgc tgatgttcgg gctataatgg ccaatgcagg ttcttcacta atggggatag     300
gaactgcaac tggaaaatca agggcaagag atgctgcatt aaatgccatc cagtcacctt     360
tactggatat tggtatagag agggctactg gaattgtttg gaacataact ggtgggactg     420
atctgacctt gtttgaggta aacacggcag cagaggttat ttatgacctc gtggacccta     480
ctgctaattt aatatttgga gcagtaatag atccatcact cagtggtcaa gtgagcataa     540
cattaattgc tactggattc aagcgtcaag aggagagtga agggaggcct ctgcaggcca     600
gtcaactcac tcaagcagac acaaccttcg gcaccaattg gcggtcttcc tctttcactg     660
atggtggttt gtttgagata ccagaattcc taaagaagag aggaggttca cgctatccga     720
gggcgtaatc ttttttcatcc taatttcttt gatcccttgc atttcttcac ccttggatat     780
acatagcatt ggtctagttc ttaggtccct gtcttgccct ttttcggatt ttagtcagag     840
ttgtgtatac agtttgttca tgaaagttta ttacttccca ctgtccagac ttatgggtct     900
aaccggaggt attgcagcat ggatgctttt cttggcatat tgaattagt ttattagctt     960
gtacagagat tcagtaatg ctgagagctt gttatagttc tttggcatgt tatagaaaat    1020
tcattatttt taaaaaaaa aaaaaaaa aaaagttcg                              1059

<210> SEQ ID NO 12
<211> LENGTH: 241
```

```
<212> TYPE: PRT
<213> ORGANISM: Glycine max

<400> SEQUENCE: 12

Gly Ile Val Thr Thr Pro Phe Ser Phe Glu Gly Arg Lys Arg Ser Ile
1               5                   10                  15

Gln Ala Gln Glu Gly Ile Thr Ala Leu Arg Asp Asn Val Asp Thr Leu
            20                  25                  30

Ile Val Ile Pro Asn Asp Lys Leu Leu Thr Ala Val Ser Gln Ser Thr
        35                  40                  45

Pro Val Thr Glu Ala Phe Asn Leu Ala Asp Asp Ile Leu Arg Gln Gly
    50                  55                  60

Val Arg Gly Ile Ser Asp Ile Ile Thr Ile Pro Gly Leu Val Asn Val
65                  70                  75                  80

Asp Phe Ala Asp Val Arg Ala Ile Met Ala Asn Ala Gly Ser Ser Leu
                85                  90                  95

Met Gly Ile Gly Thr Ala Thr Gly Lys Ser Arg Ala Arg Asp Ala Ala
            100                 105                 110

Leu Asn Ala Ile Gln Ser Pro Leu Leu Asp Ile Gly Ile Glu Arg Ala
        115                 120                 125

Thr Gly Ile Val Trp Asn Ile Thr Gly Gly Thr Asp Leu Thr Leu Phe
    130                 135                 140

Glu Val Asn Thr Ala Ala Glu Val Ile Tyr Asp Leu Val Asp Pro Thr
145                 150                 155                 160

Ala Asn Leu Ile Phe Gly Ala Val Ile Asp Pro Ser Leu Ser Gly Gln
                165                 170                 175

Val Ser Ile Thr Leu Ile Ala Thr Gly Phe Lys Arg Gln Glu Glu Ser
            180                 185                 190

Glu Gly Arg Pro Leu Gln Ala Ser Gln Leu Thr Gln Ala Asp Thr Thr
        195                 200                 205

Phe Gly Thr Asn Trp Arg Ser Ser Phe Thr Asp Gly Gly Leu Phe
    210                 215                 220

Glu Ile Pro Glu Phe Leu Lys Lys Arg Gly Gly Ser Arg Tyr Pro Arg
225                 230                 235                 240

Ala

<210> SEQ ID NO 13
<211> LENGTH: 874
<212> TYPE: DNA
<213> ORGANISM: Triticum aestivum

<400> SEQUENCE: 13
gcacgagagt gtggacactc tcattgtcat cccaaatgac aagctgttgt ctgctgtttc      60
tccaaacact cctgtcacgg aagcattcaa cttggctgat gatattcttt ggcaaggaat     120
tcgcggtatc tctgatatca ttacggttcc tgggttggtt aatgtagatt ttgcagatgt     180
gcgagccata atgcaaaatg cagggtcatc tttgatgggt ataggactg caacaggcaa      240 gtcaagagca agagacgccg ctcttaatgc cattcagtca ccactgctag atattggaat     300
tgagagggct acaggcatcg tgtggaatat cactggagga atgatttga ctttgtttga     360 ggtaaatgct gcagccgaag taatctacga tctagttgat ccaaatgcta atctgatatt     420
tggttctgtc atagacccat cactcaatgg ccaggttagc ataacattga tcgctactgg     480 cttaaacgg caggatgaag cagaaagcca caccgcaaag ggtggccagc aaatgcaagg     540
agacaatggt cgacatccat cttccacagg tggcagcaag gtggagatcc ccgagttcct     600
```

```
tcggaggaga ggaccttctc gcttcccgcg aatttgactc ttctccaggg ctccctttct    660
tagataatgc ctgttgagac tcgcccctcg tagattagat gccctcttgt aagataccag    720
acctgtagag tctagctgtt ttccgtagag gttttacttt tttgtagttt gtttgatctt    780
tctgttcttt atcttggaat gctactgcca ataatgtgta gctgtgagca tatcagtgtt    840
gtagaaaatg ttctgcaaaa aaaaaaaaaa aaaa                                874
```

```
<210> SEQ ID NO 14
<211> LENGTH: 211
<212> TYPE: PRT
<213> ORGANISM: Triticum aestivum

<400> SEQUENCE: 14
```

```
His Glu Ser Val Asp Thr Leu Ile Val Ile Pro Asn Asp Lys Leu Leu
 1               5                  10                  15

Ser Ala Val Ser Pro Asn Thr Pro Val Thr Glu Ala Phe Asn Leu Ala
            20                  25                  30

Asp Asp Ile Leu Trp Gln Gly Ile Arg Gly Ile Ser Asp Ile Ile Thr
        35                  40                  45

Val Pro Gly Leu Val Asn Val Asp Phe Ala Asp Val Arg Ala Ile Met
    50                  55                  60

Gln Asn Ala Gly Ser Ser Leu Met Gly Ile Gly Thr Ala Thr Gly Lys
65                  70                  75                  80

Ser Arg Ala Arg Asp Ala Ala Leu Asn Ala Ile Gln Ser Pro Leu Leu
                85                  90                  95

Asp Ile Gly Ile Glu Arg Ala Thr Gly Ile Val Trp Asn Ile Thr Gly
            100                 105                 110

Gly Asn Asp Leu Thr Leu Phe Glu Val Asn Ala Ala Ala Glu Val Ile
        115                 120                 125

Tyr Asp Leu Val Asp Pro Asn Ala Asn Leu Ile Phe Gly Ser Val Ile
    130                 135                 140

Asp Pro Ser Leu Asn Gly Gln Val Ser Ile Thr Leu Ile Ala Thr Gly
145                 150                 155                 160

Phe Lys Arg Gln Asp Glu Ala Glu Ser His Thr Ala Lys Gly Gly Gln
                165                 170                 175

Gln Met Gln Gly Asp Asn Gly Arg His Pro Ser Ser Thr Gly Gly Ser
            180                 185                 190

Lys Val Glu Ile Pro Glu Phe Leu Arg Arg Gly Pro Ser Arg Phe
        195                 200                 205

Pro Arg Ile
    210
```

```
<210> SEQ ID NO 15
<211> LENGTH: 514
<212> TYPE: DNA
<213> ORGANISM: Glycine max
<220> FEATURE:
<221> NAME/KEY: unsure
<222> LOCATION: (102)
<223> OTHER INFORMATION: n = a, c, g or t
<220> FEATURE:
<221> NAME/KEY: unsure
<222> LOCATION: (122)
<223> OTHER INFORMATION: n = a, c, g or t
<220> FEATURE:
<221> NAME/KEY: unsure
<222> LOCATION: (215)..(216)
<223> OTHER INFORMATION: n = a, c, g or t
<220> FEATURE:
```

-continued

```
<221> NAME/KEY: unsure
<222> LOCATION: (420)
<223> OTHER INFORMATION: n = a, c, g or t
<220> FEATURE:
<221> NAME/KEY: unsure
<222> LOCATION: (448)
<223> OTHER INFORMATION: n = a, c, g or t
<220> FEATURE:
<221> NAME/KEY: unsure
<222> LOCATION: (471)
<223> OTHER INFORMATION: n = a, c, g or t
<220> FEATURE:
<221> NAME/KEY: unsure
<222> LOCATION: (473)
<223> OTHER INFORMATION: n = a, c, g or t
<220> FEATURE:
<221> NAME/KEY: unsure
<222> LOCATION: (491)
<223> OTHER INFORMATION: n = a, c, g or t
<220> FEATURE:
<221> NAME/KEY: unsure
<222> LOCATION: (498)
<223> OTHER INFORMATION: n = a, c, g or t
<220> FEATURE:
<221> NAME/KEY: unsure
<222> LOCATION: (505)
<223> OTHER INFORMATION: n = a, c, g or t
<220> FEATURE:
<221> NAME/KEY: unsure
<222> LOCATION: (508)
<223> OTHER INFORMATION: n = a, c, g or t

<400> SEQUENCE: 15
cgatgcttca tccgctcaca aacccaaacg caaacgagct tctctcactc tcatgctctt    60
ctatattcca ccacaatgca ctcacaacct ccgtttctct cnaccccaga acaacaaaaa   120
tncctcctca acgcctaagt cgtcgtttcg ggtccgtgag atgctcttac gcttacgtag   180
ataacgccaa aattaaggtt gtcggcatcg gtggnngcgg caacaatgcc gttaatcgca   240
tgatcggtag tggtttgcag ggtgtagact tctatgcaat aaataccgat gctcaggcac   300
tgttaaattc tgctgctgag aaccctatta aaattggaga agttctgact cgtggattag   360
gtacgggcgg gaatccactt ttgggggaac aagctgcaga ggaatcaaga gatgctattn   420
ctgatgctct taaaggatca gatttggngt ttataacggc tgggatgggt ngnggaaccg   480
ggtctggtgc ngacccantt gtagnccaaa tatc                              514

<210> SEQ ID NO 16
<211> LENGTH: 128
<212> TYPE: PRT
<213> ORGANISM: Glycine max
<220> FEATURE:
<221> NAME/KEY: UNSURE
<222> LOCATION: (30)
<223> OTHER INFORMATION: Xaa = any amino acid
<220> FEATURE:
<221> NAME/KEY: UNSURE
<222> LOCATION: (98)
<223> OTHER INFORMATION: Xaa = any amino acid
<220> FEATURE:
<221> NAME/KEY: UNSURE
<222> LOCATION: (107)
<223> OTHER INFORMATION: Xaa = any amino acid
<220> FEATURE:
<221> NAME/KEY: UNSURE
<222> LOCATION: (115)
<223> OTHER INFORMATION: Xaa = any amino acid
<220> FEATURE:
<221> NAME/KEY: UNSURE
<222> LOCATION: (124)
<223> OTHER INFORMATION: Xaa = any amino acid
<220> FEATURE:
<221> NAME/KEY: UNSURE
```

```
<222> LOCATION: (126)..(127)
<223> OTHER INFORMATION: Xaa = any amino acid

<400> SEQUENCE: 16

Gln Arg Leu Ser Arg Arg Phe Gly Ser Val Arg Cys Ser Tyr Ala Tyr
 1               5                  10                  15

Val Asp Asn Ala Lys Ile Lys Val Val Gly Ile Gly Gly Xaa Gly Asn
             20                  25                  30

Asn Ala Val Asn Arg Met Ile Gly Ser Gly Leu Gln Gly Val Asp Phe
         35                  40                  45

Tyr Ala Ile Asn Thr Asp Ala Gln Ala Leu Leu Asn Ser Ala Ala Glu
     50                  55                  60

Asn Pro Ile Lys Ile Gly Glu Val Leu Thr Arg Gly Leu Gly Thr Gly
 65                  70                  75                  80

Gly Asn Pro Leu Leu Gly Glu Gln Ala Ala Glu Ser Arg Asp Ala
                 85                  90                  95

Ile Xaa Asp Ala Leu Lys Gly Ser Asp Leu Xaa Phe Ile Thr Ala Gly
            100                 105                 110

Met Gly Xaa Gly Thr Gly Ser Gly Ala Asp Pro Xaa Val Xaa Xaa Ile
        115                 120                 125

<210> SEQ ID NO 17
<211> LENGTH: 644
<212> TYPE: DNA
<213> ORGANISM: Triticum aestivum
<220> FEATURE:
<221> NAME/KEY: unsure
<222> LOCATION: (514)
<223> OTHER INFORMATION: n = a, c, g or t
<220> FEATURE:
<221> NAME/KEY: unsure
<222> LOCATION: (538)
<223> OTHER INFORMATION: n = a, c, g or t
<220> FEATURE:
<221> NAME/KEY: unsure
<222> LOCATION: (599)
<223> OTHER INFORMATION: n = a, c, g or t
<220> FEATURE:
<221> NAME/KEY: unsure
<222> LOCATION: (601)
<223> OTHER INFORMATION: n = a, c, g or t
<220> FEATURE:
<221> NAME/KEY: unsure
<222> LOCATION: (603)
<223> OTHER INFORMATION: n = a, c, g or t
<220> FEATURE:
<221> NAME/KEY: unsure
<222> LOCATION: (615)
<223> OTHER INFORMATION: n = a, c, g or t
<220> FEATURE:
<221> NAME/KEY: unsure
<222> LOCATION: (620)..(621)
<223> OTHER INFORMATION: n = a, c, g or t
<220> FEATURE:
<221> NAME/KEY: unsure
<222> LOCATION: (627)
<223> OTHER INFORMATION: n = a, c, g or t

<400> SEQUENCE: 17
cctcccctct cctcccggcc acctctcccc acgcccattc ccgcacggc caagggaaaa      60 tggcgccgtc cacctcgtcg gcctccgccc tcctccacct cccgggtctg cctcccggg     120 gaccccatag aggcgggtgc cggaaccacc cgcggcggcc gcgccatgcg gccgtgcggt    180
gctccttcgc gttcgcgccc gtggagacgc gaggataaa ggtcgtgggc gtaggtggcg     240
gcggcaacaa cgccgtcaac cgcatgatcg gcagcggcct ccagggaatc gagttttatg    300
```

-continued

```
ctataaacac agactcccag gctcttgtga attcccaggc gcaacatccg ctacaaattg      360
gagaacaatt gactcgtggg ctgggtactg gtggaaatcc taatttggga gaacaagctg      420
ccgaggaatc aaaggaagtg atagtaatgc ctccgagatt ctgaccttgt ctcataaagc      480
tgggatggga agtgtactgg tccgtgctgc tcantgttcc aaatacaaag gaggcggnta      540
tctacgtcgt gttgtactac attaacttca aggagaacgt ctcaaggatc aacatgggna      600
ntnaagatgt taaancgatn natcaanatc gttaaaatgc gata                      644
```

<210> SEQ ID NO 18
<211> LENGTH: 94
<212> TYPE: PRT
<213> ORGANISM: Triticum aestivum

<400> SEQUENCE: 18

```
Arg His Ala Ala Val Arg Cys Ser Phe Ala Phe Ala Pro Val Glu Thr
 1               5                  10                  15

Ala Arg Ile Lys Val Val Gly Val Gly Gly Gly Asn Asn Ala Val
             20                  25                  30

Asn Arg Met Ile Gly Ser Gly Leu Gln Gly Ile Glu Phe Tyr Ala Ile
         35                  40                  45

Asn Thr Asp Ser Gln Ala Leu Val Asn Ser Gln Ala Gln His Pro Leu
     50                  55                  60

Gln Ile Gly Glu Gln Leu Thr Arg Gly Leu Gly Thr Gly Gly Asn Pro
 65                  70                  75                  80

Asn Leu Gly Glu Gln Ala Ala Glu Glu Ser Lys Glu Val Ile
                 85                  90
```

<210> SEQ ID NO 19
<211> LENGTH: 449
<212> TYPE: DNA
<213> ORGANISM: Oryza sativa
<220> FEATURE:
<221> NAME/KEY: unsure
<222> LOCATION: (418)
<223> OTHER INFORMATION: n = a, c, g or t

<400> SEQUENCE: 19

```
cctcattgtc atcccaaatg acaagctgtt gtctgctgtt tctccaaata ctccagtaac       60
cgaagcattc aacttggctg atgatattct tcgacaagga attcgtggta tctctgatat      120
tatcacggtt cctgggttgg ttaatgttga ttttgctgat gttcgagcca tcatgcaaaa      180
tgcaggctca tccttgatgg gtattggaac ggctacaggg aagtcaagag caagagatgc      240
tgctcttaat gccattcagt caccactgct agacattgga attgaaagag ctacaggcat      300
tgtgtggaat atcactgggg gaagctgata tgactttgtt tgagggaat tctgctgctg       360 agatcatcta tgaccttgtt gatccaaatg ctaaacctga tatttggtgc tgtcaaanac      420
ccatcactca atgggcaaag tgagcataa                                         449
```

<210> SEQ ID NO 20
<211> LENGTH: 130
<212> TYPE: PRT
<213> ORGANISM: Oryza sativa

<400> SEQUENCE: 20

```
Leu Ile Val Ile Pro Asn Asp Lys Leu Leu Ser Ala Val Ser Pro Asn
 1               5                  10                  15

Thr Pro Val Thr Glu Ala Phe Asn Leu Ala Asp Asp Ile Leu Arg Gln
             20                  25                  30
```

-continued

```
Gly Ile Arg Gly Ile Ser Asp Ile Ile Thr Val Pro Gly Leu Val Asn
         35                  40                  45
Val Asp Phe Ala Asp Val Arg Ala Ile Met Gln Asn Ala Gly Ser Ser
     50                  55                  60
Leu Met Gly Ile Gly Thr Ala Thr Gly Lys Ser Arg Ala Arg Asp Ala
 65                  70                  75                  80
Ala Leu Asn Ala Ile Gln Ser Pro Leu Leu Asp Ile Gly Ile Glu Arg
                 85                  90                  95
Ala Thr Gly Ile Val Trp Asn Ile Thr Gly Glu Ala Asp Met Thr Leu
            100                 105                 110
Phe Glu Gly Asn Ser Ala Ala Glu Ile Ile Tyr Asp Leu Val Asp Pro
        115                 120                 125
Asn Ala
    130
```

```
<210> SEQ ID NO 21
<211> LENGTH: 510
<212> TYPE: DNA
<213> ORGANISM: Glycine max
<220> FEATURE:
<221> NAME/KEY: unsure
<222> LOCATION: (24)
<223> OTHER INFORMATION: n = a, c, g or t
<220> FEATURE:
<221> NAME/KEY: unsure
<222> LOCATION: (327)..(328)
<223> OTHER INFORMATION: n = a, c, g or t
<220> FEATURE:
<221> NAME/KEY: unsure
<222> LOCATION: (374)
<223> OTHER INFORMATION: n = a, c, g or t
<220> FEATURE:
<221> NAME/KEY: unsure
<222> LOCATION: (378)
<223> OTHER INFORMATION: n = a, c, g or t
<220> FEATURE:
<221> NAME/KEY: unsure
<222> LOCATION: (402)
<223> OTHER INFORMATION: n = a, c, g or t

<400> SEQUENCE: 21
ttggtattgt caccacccct ttcncgtttg aagggagaaa gagatctatt caagcccaag      60
aaggaattac agccttaaga gataatgttg acacgcttat agttattcca aatgacaagc     120
tactaacggc agtttctcaa tctacccctg taactgaagc attcaatctg gctgatgata     180
ttcttcgaca gggtgttcgt ggcatatctg atattattac ataccagggg ttggtgaatg     240
tacattttgc tgatgttcgg gctataatgg ccaatgcagg ttcttcacta atggggatag     300
gaactgcaac tggaaaatca agggcannag atgctgcatt aaatgccatc cagtcacctt     360
tactggatat tggnatanag agggctactg gaattgtttg gnacataact ggtgggactg     420
atctgacctt gtttgaggta aacacggcag caaaaggtat tatgacctcc gtggccccta     480
ctgctaatta atatttggag caagtaataa                                      510
```

```
<210> SEQ ID NO 22
<211> LENGTH: 162
<212> TYPE: PRT
<213> ORGANISM: Glycine max
<220> FEATURE:
<221> NAME/KEY: UNSURE
<222> LOCATION: (8)
<223> OTHER INFORMATION: Xaa = any amino acid
<220> FEATURE:
<221> NAME/KEY: UNSURE
```

```
<222> LOCATION: (109)
<223> OTHER INFORMATION: Xaa = any amino acid
<220> FEATURE:
<221> NAME/KEY: UNSURE
<222> LOCATION: (126)
<223> OTHER INFORMATION: Xaa = any amino acid
<220> FEATURE:
<221> NAME/KEY: UNSURE
<222> LOCATION: (134)
<223> OTHER INFORMATION: Xaa = any amino acid

<400> SEQUENCE: 22

Gly Ile Val Thr Thr Pro Phe Xaa Phe Glu Gly Arg Lys Arg Ser Ile
  1               5                  10                  15

Gln Ala Gln Glu Gly Ile Thr Ala Leu Arg Asp Asn Val Asp Thr Leu
             20                  25                  30

Ile Val Ile Pro Asn Asp Lys Leu Leu Thr Ala Val Ser Gln Ser Thr
         35                  40                  45

Pro Val Thr Glu Ala Phe Asn Leu Ala Asp Asp Ile Leu Arg Gln Gly
     50                  55                  60

Val Arg Gly Ile Ser Asp Ile Ile Thr Ile Pro Gly Leu Val Asn Val
 65                  70                  75                  80

His Phe Ala Asp Val Arg Ala Ile Met Ala Asn Ala Gly Ser Ser Leu
                 85                  90                  95

Met Gly Ile Gly Thr Ala Thr Gly Lys Ser Arg Ala Xaa Asp Ala Ala
            100                 105                 110

Leu Asn Ala Ile Gln Ser Pro Leu Leu Asp Ile Gly Ile Xaa Arg Ala
        115                 120                 125

Thr Gly Ile Val Trp Xaa Ile Thr Gly Gly Thr Asp Leu Thr Leu Phe
    130                 135                 140

Glu Val Asn Thr Ala Ala Lys Gly Ile Met Thr Ser Val Ala Pro Thr
145                 150                 155                 160

Ala Asn

<210> SEQ ID NO 23
<211> LENGTH: 604
<212> TYPE: DNA
<213> ORGANISM: Triticum aestivum
<220> FEATURE:
<221> NAME/KEY: unsure
<222> LOCATION: (365)
<223> OTHER INFORMATION: n = a, c, g or t
<220> FEATURE:
<221> NAME/KEY: unsure
<222> LOCATION: (382)
<223> OTHER INFORMATION: n = a, c, g or t
<220> FEATURE:
<221> NAME/KEY: unsure
<222> LOCATION: (386)
<223> OTHER INFORMATION: n = a, c, g or t
<220> FEATURE:
<221> NAME/KEY: unsure
<222> LOCATION: (402)
<223> OTHER INFORMATION: n = a, c, g or t
<220> FEATURE:
<221> NAME/KEY: unsure
<222> LOCATION: (419)
<223> OTHER INFORMATION: n = a, c, g or t
<220> FEATURE:
<221> NAME/KEY: unsure
<222> LOCATION: (427)
<223> OTHER INFORMATION: n = a, c, g or t
<220> FEATURE:
<221> NAME/KEY: unsure
<222> LOCATION: (436)
<223> OTHER INFORMATION: n = a, c, g or t
<220> FEATURE:
```

-continued

```
<221> NAME/KEY: unsure
<222> LOCATION: (441)
<223> OTHER INFORMATION: n = a, c, g or t
<220> FEATURE:
<221> NAME/KEY: unsure
<222> LOCATION: (446)
<223> OTHER INFORMATION: n = a, c, g or t
<220> FEATURE:
<221> NAME/KEY: unsure
<222> LOCATION: (460)
<223> OTHER INFORMATION: n = a, c, g or t
<220> FEATURE:
<221> NAME/KEY: unsure
<222> LOCATION: (476)
<223> OTHER INFORMATION: n = a, c, g or t
<220> FEATURE:
<221> NAME/KEY: unsure
<222> LOCATION: (484)..(485)
<223> OTHER INFORMATION: n = a, c, g or t
<220> FEATURE:
<221> NAME/KEY: unsure
<222> LOCATION: (490)
<223> OTHER INFORMATION: n = a, c, g or t
<220> FEATURE:
<221> NAME/KEY: unsure
<222> LOCATION: (511)
<223> OTHER INFORMATION: n = a, c, g or t
<220> FEATURE:
<221> NAME/KEY: unsure
<222> LOCATION: (517)
<223> OTHER INFORMATION: n = a, c, g or t
<220> FEATURE:
<221> NAME/KEY: unsure
<222> LOCATION: (534)
<223> OTHER INFORMATION: n = a, c, g or t
<220> FEATURE:
<221> NAME/KEY: unsure
<222> LOCATION: (536)
<223> OTHER INFORMATION: n = a, c, g or t
<220> FEATURE:
<221> NAME/KEY: unsure
<222> LOCATION: (547)..(548)
<223> OTHER INFORMATION: n = a, c, g or t
<220> FEATURE:
<221> NAME/KEY: unsure
<222> LOCATION: (554)
<223> OTHER INFORMATION: n = a, c, g or t
<220> FEATURE:
<221> NAME/KEY: unsure
<222> LOCATION: (576)
<223> OTHER INFORMATION: n = a, c, g or t
<220> FEATURE:
<221> NAME/KEY: unsure
<222> LOCATION: (598)..(599)
<223> OTHER INFORMATION: n = a, c, g or t
<220> FEATURE:
<221> NAME/KEY: unsure
<222> LOCATION: (604)
<223> OTHER INFORMATION: n = a, c, g or t

<400> SEQUENCE: 23
agtgtggaca ctctcattgt catcccaaat gacaagctgt tgtctgctgt ttctccaaac    60
actcctgtca cggaagcatt caacttggct gatgatattc tttggcaagg aattcgcggt   120
atctctgata tcattacggt tcctgggttg gttaatgtag attttgcaga tgtgcgagcc   180
ataatgcaaa atgcagggtc atctttgatg ggtatagggga ctgcaacagg caagtcaaga   240
gcaagagacg ccgctcttaa tgccattcag tcaccactgc tagatattgg aattgaaagg   300
gctacaggca tcgtgtggaa tatcactgga ggaaatgatt tgactttgtt tgaggtaaat   360
gctgnagccg aagtaatcaa cnatcnaatt gttcaaaatg cnacctgaat tggttctgnc   420
atagacnatc actcanggc nagttngaaa aattgttccn acggtttaaa ggaggntacc   480
aaanncaccn caaggggggca aattcaggaa nagggcnaca tcactcaagg gggnanaggg   540
```

```
gttcccnntc tcgngaagct ccctcccatt gcctcnagcc cttcaaaagc ttaacccnna    600 atan                                                                 604
```

<210> SEQ ID NO 24
<211> LENGTH: 126
<212> TYPE: PRT
<213> ORGANISM: Triticum aestivum
<220> FEATURE:
<221> NAME/KEY: UNSURE
<222> LOCATION: (122)
<223> OTHER INFORMATION: Xaa = any amino acid

<400> SEQUENCE: 24

```
Ser Val Asp Thr Leu Ile Val Ile Pro Asn Asp Lys Leu Leu Ser Ala
 1               5                  10                  15

Val Ser Pro Asn Thr Pro Val Thr Glu Ala Phe Asn Leu Ala Asp Asp
            20                  25                  30

Ile Leu Trp Gln Gly Ile Arg Gly Ile Ser Asp Ile Ile Thr Val Pro
        35                  40                  45

Gly Leu Val Asn Val Asp Phe Ala Asp Val Arg Ala Ile Met Gln Asn
    50                  55                  60

Ala Gly Ser Ser Leu Met Gly Ile Gly Thr Ala Thr Gly Lys Ser Arg
65                  70                  75                  80

Ala Arg Asp Ala Ala Leu Asn Ala Ile Gln Ser Pro Leu Leu Asp Ile
                85                  90                  95

Gly Ile Glu Arg Ala Thr Gly Ile Val Trp Asn Ile Thr Gly Gly Asn
            100                 105                 110

Asp Leu Thr Leu Phe Glu Val Asn Ala Xaa Ala Glu Val Ile
        115                 120                 125
```

US 6,812,382 B1

PLANT GENES ENCODING CHLOROPLAST DIVISION PROTEINS

This application claims priority benefit of U.S. Provisional Application No. 60/119,419 filed Feb. 10, 1999.

FIELD OF THE INVENTION

This invention is in the field of plant molecular biology. More specifically, this invention pertains to nucleic acid fragments encoding proteins involved in chloroplast division in plants and seeds.

BACKGROUND OF THE INVENTION

In plants plastid organelles harbor several metabolic pathways essential for plant growth, development and viability. Specifically, plastids contain the metabolic pathways for photosynthesis, the synthesis of various amino acids, lipids and plant growth regulatory hormones (Mullet, J. E. (1988) *Annu. Rev. Plant Physiol. Plant Mol Biol.* 39:475–502). During cell division plastids divide and segregate to daughter cells in a manner that insures that each daughter cell receives sufficient numbers of plastids to provide the cell with efficient photosynthetic and biosynthetic capabilities. Plastids appear to divide by a binary fission mechanism that involves two contractile rings, one on the stromal face of the inner envelope and one on the cytosolic face of the outer envelope (Kuroiwa, T., et al., (1998) *Int. Rev. Cyto.* 181:1–41). However, little is known about the exact nature of these rings or the precise mechanism of plastid division.

A genetic study of plastid division in Arabidopsis has revealed several arc mutations (accumulation and replication of chloroplasts) that define at least seven nuclear genes important in the control of plastid division (Pyke, K. A., (1997) *Am. J Bot.* 84:1017–1027). Osteryoung et al. have discovered, in the nuclear genome of Arabidopsis, a homolog of the bacterial cell division gene ftsZ. In bacteria defects in the ftsZ gene (for filament temperature-sensitive) cause filament formation and incomplete septum formation at the restrictive temperature (Osteryoung, K. W., et al., (1995) *Nature* 376:473–474. The encoded FtsZ protein appears to be part of the cell division apparatus, specifically a cytoskelatal component of the contractile ring (Osteryoung, K. W., et al., (1998) *The Plant Cell* 10:1991–2004) and Strepp et al. reports that mutations in the FtsZ gene resulted in the disruption of chloroplast division (Strepp, R., et al., (1998) *Proc. Natl. Acad. Sci.* 95:4368–4373).

Recent studies indicate that Arabidopsis contains two FtsZ genes one localized to the cytosol (FtsZ2) and one to the chloroplast (FtsZ1). Inhibition of either causes a severe decrease in the numbers of chloroplasts in Arabidopsis leaf cells (Osteryoung, K., et al., (1998) *The Plant Cell* 10:1991–2004). Thus the two FtsZ genes are both essential for chloroplast division and appear to play distinct roles in the division process. The Osteryoung studies indicate further that plant FtsZ genes are grouped into two families and that the FtsZ proteins within a family share amino acid sequence identities ranging from 76 to 91% however between families the similarity declines to 61%.

There is a great deal of interest in identifying the genes that encode proteins involved in plastid division in plants. These gene may be used to enhance plastid transformation. For example, if gene expression of the ftsZ genes could be inhibited, plants with 1–3 very large chloroplasts per cell would be produced. By decreasing the number of chloroplasts per cell and increasing the size of each chloroplast a much better recipient cell for plastid transformation would result. Furthermore, because the FtsZ proteins are essential for chloroplast division, their inhibition could significantly decrease the, efficiency of photosynthesis and other metabolic pathways. Accordingly, the availability of nucleic acid sequences encoding all or a portion of a FtsZ protein would facilitate studies to better understand chloroplast division in plants and provide genetic tools to inhibit or otherwise alter chloroplast division in plants.

SUMMARY OF THE INVENTION

The present invention relates to isolated polynucleotides comprising a nucleotide sequence encoding a polypeptide of at least 145 amino acids that has at least 90% identity based on the Clustal method of alignment when compared to a polypeptide selected from the group consisting of corn cytosol and chloroplast associated FtsZ polypeptides of SEQ ID NOs:2 and 8, a rice cytosol FtsZ polypeptide of SEQ ID NO:10, a soybean chloroplast associated FtsZ polypeptide of SEQ ID NO:4, and wheat cytosol and chloroplast associated FtsZ polypeptides of SEQ ID NOs:6 and 14. The present invention also relates to an isolated polynucleotide comprising the complement of the nucleotide sequences described above.

The present invention also relates to isolated polynucleotides comprising a nucleotide sequence encoding a polypeptide of at least 241 amino acids that has at least 90% identity based on the Clustal method of alignment when compared to a soybean cytosol associated FtsZ polypeptide of SEQ ID NO:12. The present invention also relates to an isolated polynucleotide comprising the complement of the nucleotide sequences described above.

The present invention also relates to isolated polynucleotides comprising a nucleotide sequence encoding a polypeptide of at least 94 amino acids that has at least 90% identity based on the Clustal method of alignment when compared to a polypeptide selected from the group consisting of SEQ ID NOs:16, 18, 20, 22 and 24. The present invention also relates to an isolated polynucleotide comprising the complement of the nucleotide sequences described above.

It is preferred that the isolated polynucleotides of the claimed invention consists of a nucleic acid sequence selected from the group consisting of SEQ ID NOs:1, 3, 5, 7, 9, 11, 13, 15, 17, 19, 21 and 23 that codes for the polypeptide selected from the group consisting of SEQ ID NOs:2, 4, 6, 8, 10, 12, 14, 16, 18, 20, 22 and 24. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a cytosol and chloroplast associated FtsZ polypeptide of at least 145 amino acids comprising at least 90% homology based on the Clustal method of alignment compared to a polypeptide selected from the group consisting of SEQ ID NOs:2, 4, 6, 8, 10 and 14.

The present invention relates to a cytosol associated FtsZ polypeptides polypeptide of at least 241 amino acids comprising at least 90% homology based on the Clustal method of alignment compared to a polypeptide of SEQ ID NO:12.

The present invention relates to a method of selecting an isolated polynucleotide that affects the level of expression of a cytosol or chloroplast associated FtsZ polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a cytosol or chloroplast associated FtsZ polypeptide in the host cell containing the isolated polynucleotide; and (d) comparing the level of a cytosol or chloroplast associated FtsZ polypeptide in the host cell containing the isolated polynucleotide with the level of a cytosol or chloroplast associated FtsZ polypeptide in the host cell that does not contain the isolated polynucleotide.

The present invention relates to a method of obtaining a nucleic acid fragment encoding a substantial portion of a cytosol or chloroplast associated FtsZ polypeptide gene, preferably a plant cytosol or chloroplast associated FtsZ polypeptide gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, and the complement of such nucleotide sequences; and amplifying a nucleic acid fragment (preferably a cDNA inserted in a cloning vector) using the oligonucleotide primer. The amplified nucleic acid fragment preferably will encode a portion of a cytosol or chloroplast associated FtsZ amino acid sequence.

The present invention also relates to a method of obtaining a nucleic acid fragment encoding all or a substantial portion of the amino acid sequence encoding a cytosol or chloroplast associated FtsZ polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The present invention relates to a composition, such as a hybridization mixture, comprising an isolated polynucleotide of the present invention.

The present invention relates to an isolated polynucleotide of the present invention comprising at least one of 30 contiguous nucleotides derived from a nucleic acid sequence selected from the group consisting of SEQ ID NOs:1, 3, 5, 7, 9, 11, 13, 15, 17, 19, 21 and 23 or the complement thereof.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the cytosol or chloroplast associated FtsZ polynucleotide in an amount sufficient to complement a null mutant with reduced chloroplast numbers to provide a positive selection means.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:3, 5, 9, 11 and 13 and amino acid sequences SEQ ID NOs:4, 6, 10, 12, and 14 were determined by further sequence analysis of cDNA clones encoding the amino acid sequences set forth in SEQ ID NOs:16, 18, 20, 22 and 24. Nucleotide SEQ ID NOs:15, 17, 19, 21 and 23 and amino acid SEQ ID NOs:16, 18, 20, 22 and 24 were presented in a U.S. Provisional Application No. 60/119,419, filed Feb. 10, 1999.

The sequence descriptions and Sequence Listing attached hereto comply with the rules governing nucleotide and/or amino acid sequence disclosures in patent applications as set forth in 37 C.F.R. §1.821–1.825.

TABLE 1

Proteins Involved in Chloroplast Division

| | | SEQ ID NO: | |
|---|---|---|---|
| Protein | Clone Designation | (Nucleotide) | (Amino Acid) |
| Chloroplast Associted FtsZ | p0021.cperb30rb:EST | 1 | 2 |
| Chloroplast Associted FtsZ | ses2w.pk0008.h8:FIS | 3 | 4 |
| Chloroplast Associted FtsZ | wlm24.pk0013.d6:FIS | 5 | 6 |
| Cytosol Associted FtsZ | ceb5.pk0049.b9:EST | 7 | 8 |
| Cytosol Associted FtsZ | rsl1n.pk009.h15:FIS | 9 | 10 |
| Cytosol Associted FtsZ | s12.pk130.o19:FIS | 11 | 12 |
| Cytosol Associted FtsZ | wr1.pk0108.c6: FIS | 13 | 14 |
| Chloroplast Associted FtsZ | ses2w.pk0008.h8:EST | 15 | 16 |
| Chloroplast Associted FtsZ | wlm24.pk0013.d6:EST | 17 | 18 |
| Cytosol Associted FtsZ | rsl1n.pk009.h15:EST | 19 | 20 |
| Cytosol Associted FtsZ | sl2.pk130.o19:EST | 21 | 22 |
| Cytosol Associted FtsZ | wr1.pk0108.c6:EST | 23 | 24 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, or the complement of such sequences.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, and the complement of such nucleotide sequences may be used in methods of selecting an isolated polynucleotide that affects the expression of a polypeptide (cytosol or chloroplast associated FtsZ) in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithm's commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or.cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed MRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the MRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the hucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several proteins involved in chloroplast division have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other cytosol or chloroplast associated FtsZ proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as cytosol or chloroplast associated FtsZ proteins) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide(cytosol or chloroplast associated FtsZ).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cPNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the number of chloroplasts in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired! phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded protein involved in chloroplast division. An example of a vector for high level expression of the instant polypeptides in a bacterial host is provided (Example 7).

All or a substantial portion of the nucleic acid fragments of the instant invention may also be used as probes for genetically and physically mapping the genes that they are a part of, and as markers for traits linked to those genes. Such information' may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nulcleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled' in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLE 1

Composition of CDNA Libraries, Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| ceb5 | Corn Embryo 30 Days After Pollination | ceb5.pk0049.b9 |
| p0021 | Corn Pericarp 11 Days After Pollination | p0021.cperb30rb |
| rsl1n | Rice 15-Day-Old Seedling* | rsl1n.pk009.h15 |
| ses2w | Soybean Embryogenic Suspension 2 Weeks After Subculture | ses2w.pk0008.h8 |
| sl2 | Soybean Two-Week-Old Developing Seedlings Treated With 2.5 ppm chlorimuron | sl2.pk130.o19 |
| wlm24 | Wheat Seedlings 24 Hours After Inoculation With *Erysiphe graminis f. sp tritici* | wlm24.pk0013.d6 |
| wr1 | Wheat Root From 7 Day Old Seedling | wr1.pk0108.c6 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAPT™XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

EXAMPLE 2

Identification of cDNA Clones cDNA clones encoding proteins involved in chloroplast division were identified by conducting BLAST (Basic Local Alignment Search Tool; Altschul et al. (1993) *J. Mol. Biol.* 215:403410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The CDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a CDNA sequence to a sequence contained in the searched databases merely by chance as calculated by BLAST are reported herein as "plog" values, which represent the negative of the logarithm of the reported P-value. Accordingly, the greater the plog value, the greater the likelihood that the CDNA sequence and the BLAST "hit" represent homologous proteins.

EXAMPLE 3

Characterization of cDNA Clones Encoding Chloroplast Associated FtsZ Proteins The BLASTX search using the EST sequences from clones listed in Table 3 revealed similarity of the polypeptides encoded by the cDNAs to chloroplast associated FtsZ proteins from *Arabidopsis thaliana* (NCBI Identifier No. gi 2494610) and *Pisum sativum* (NCBI Identifier No. gi 3116020). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to *Arabidopsis thaliana* and *Pisum sativum* FtsZ Proteins

| Clone | Status | BLAST pLog Score |
|---|---|---|
| p0021.cperb30rb: | EST | 43.15 (gi 2494610) |
| ses2w.pk0008.h8: | FIS | >254.00 (gi 3116020) |
| wlm24.pk0013.d6 | FIS | 163.00 (gi 2494610) |

The data in Table 4 represents a calculation of the percent identity of the amino acid sequences set forth in SEQ ID NOs:2, 4 and 6 and the *Arabidopsis thaliana* and *Pisum sativum* sequences. The percent identity between SEQ ID NOs:2, 4and 6 ranged between 60 to 80%.

TABLE 4

Percent Identity of Amino Acid Sequences Deduced From the Nucleotide Sequences of cDNA Clones Encoding Polypeptides Homologous to *Arabidopsis thaliana* and *Pisum sativum* FtsZ Proteins

| SEQ ID NO. | Percent Identity to |
|---|---|
| 2 | 50% (gi 2494610) |
| 4 | 87% (gi 3116020) |
| 6 | 70% (gi 2494610) |

Sequence alignments and percent identity calculations were performed using the Megalign program of the LASER-GENE bioinformatics computing suite (DNASTAR Inc., Madison, Wis). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a chloroplast associated FtsZ protein. These sequences represent the first corn, soybean and wheat sequences encoding chloroplast associated FtsZ proteins.

EXAMPLE 4

Characterization of cDNA Clones Encoding Cytosol Associated FtsZ Proteins

The BLASTX search using the EST sequences from clones listed in Table 5 revealed similarity of the polypeptides encoded by the cDNAs to cytosol associated FtsZ proteins from *Arabidopsis thaliana* (NCBI Identifier No. gi 3608495) and *Gentiana lutea* (NCBI Identifier No. gi 6685070). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides Homologous to *Arabidopsis thaliana* and *Gentiana lutea* Cytosol Associated FtsZ Proteins

| Clone | Status | BLAST pLog Score |
|---|---|---|
| ceb5.pk0049.b9 | EST | 76.40 (gi 6685070) |
| rsl1n.pk009.h15 | FIS | 90.52 (gi 3608495) |
| sl2.pk130.o19 | FIS | 110.00 (gi 3608495) |
| wr1.pk0108.c6 | FIS | 87.70 (gi 3608495) |

The data in Table 6 represents a calculation of the percent identity of the amino acid sequences set forth in SEQ ID NOs:8, 10, 12 and 14 and the *Arabidopsis thaliana* and *Gentiana lutea* sequences. The percent identity between SEQ ID NOs:8, 10, 12 and 14 ranged from 80 to 92%.

TABLE 6

Percent Identity of Amino Acid Sequences Deduced From the Nucleotide Sequences of cDNA Clones Encoding Polypeptides Homologous to *Arabidopsis thaliana* and *Gentiana lutea* Cytosol Associated FtsZ Proteins

| SEQ ID NO. | Percent Identity to |
|---|---|
| 8 | 86% (gi 6685070) |
| 10 | 80% (gi 3608495) |
| 12 | 84% (gi 3608495) |
| 14 | 77% (gi 3608495) |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a cytosol associated FtsZ protein. These sequences represent the first corn, rice, soybean and wheat sequences encoding cytosol associated FtsZ proteins.

EXAMPLE 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 sum in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

EXAMPLE 6

Expression of Chimeric Genes in Dicot Cells

A seed-specific expression cassette composed of the promoter and transcription terminator from the gene encoding the 0 subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with pheno/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding an FtsZ polypeptide having plastid division activity, wherein the polypeptide has an amino acid sequence of at least 90% sequence identity, based on the Clustal alignment method, when compared to SEQ ID NO:4; or
   (b) the complement of the nucleotide sequence, wherein the complement and the nucleotide sequence contain the same number of nucleotides and are 100% complementary.

2. The polynucleotide of claim 1, wherein the amino acid sequence of the polypeptide has at least 95% sequence identity, based on the Clustal alignment method, when compared to SEQ ID NO:4.

3. The polynucleotide of claim 1, wherein the amino acid sequence of the polypeptide comprises SEQ ID NO:4.

4. The polynucleotide of claim 1, wherein the nucleotide sequence comprises SEQ ID NO:3.

5. A vector comprising the polynucleotide of claim 1.

6. A recombinant DNA construct comprising the polynucleotide of claim 1 operably linked to at least one regulatory sequence.

7. A method for transforming a cell comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *